US006552191B1

(12) United States Patent
Zhou et al.

(10) Patent No.: US 6,552,191 B1
(45) Date of Patent: Apr. 22, 2003

(54) METHOD OF EXTRACTING TETRODOTOXIN

(75) Inventors: Maoqing Zhou, Nanning (CN); Frank Hay Kong Shum, North Point (HK)

(73) Assignee: Wex Medical Instrumentation Co., Ltd., Hong Kong (HK)

( * ) Notice: Subject to any disclaimer, the term of this patent is extended or adjusted under 35 U.S.C. 154(b) by 0 days.

(21) Appl. No.: 09/695,711

(22) Filed: Oct. 25, 2000

(30) Foreign Application Priority Data

Sep. 18, 2000 (CN) .................................... 00 1 24516.3

(51) Int. Cl.[7] ............................................ C07D 491/20
(52) U.S. Cl. ...................................................... 544/247
(58) Field of Search ......................................... 544/247

(56) References Cited

U.S. PATENT DOCUMENTS

| | | | | |
|---|---|---|---|---|
| 4,857,653 | A | 8/1989 | Colin et al. | 549/111 |
| 4,924,011 | A | 5/1990 | Denis et al. | 549/510 |
| 5,019,504 | A | 5/1991 | Christen et al. | 435/123 |
| 5,336,785 | A | 8/1994 | Holton | 549/214 |
| 5,451,392 | A | 9/1995 | Strobel et al. | 424/181 |
| 5,475,120 | A | 12/1995 | Rao | 549/510 |
| 5,478,736 | A | 12/1995 | Nair | 435/123 |

OTHER PUBLICATIONS

Goto et al, J. Chem. Soc. Japan, 1964, 85, 2–9).*

Xinfu et al, Advances in the Study of Tetrodotoxin, 1979, 1–8.*

Pan Xinfu et al., *Aquatic Product Institute of Hebel, Advances in the Study of Tetrodotoxin*, pp 1–8, (1979).

Toshio Goto et al., *J. Chem. Soc. Japan, Extraction and Purification of the Puffer Fish Toxin Tetrodotoxin*, vol. 85, pp508, (1964).

Munetomo Nakamura et al., *Toxicon, Tetrodotoxin Derivatives in Puffer Fish*, vol. 23, pp271–276, (1985).

Toshio Goto et al., *Tetrodotoxin, Tetrahedron*, vol. 21, pp2059–2088, (1965).

Takeshi Yasumoto et al., *Agric. Biol. Chem., Fluorometric Determination of Tetrodotoxin by High Performance Liquid Chromatography*, vol. 49, pp3077–3080, (1985).

Huilan Zhao et al., *China J. Hygiene Examination, Study on the Method of Detecting Tetrodotoxin by Reverse Phase HPLC*, vol. 49, pp263–265, (1994).

Y. Hashimoto, "Marine Toxins and Other Bioactive Marine Metobolites", pp. 71–91 c. 1979 by Japan Society Press.

H. Kakisawa et al., J. Chem. Soc. Japan, vol. 80, pp. 1483–1487 (1959) (abstract from Chem. Abstr. vol. 55, pp. 3542).

A. Yokoo et al., J. Chem Soc. Japan, vol. 71, pp. 590–592 (1950) (abstract from Chem. Abstr. vol. 45, pp. 6760).

* cited by examiner

*Primary Examiner*—Mukund Shah
*Assistant Examiner*—Thomas McKenzie
(74) *Attorney, Agent, or Firm*—Birch, Stewart, Kolasch & Birch , LLP

(57) ABSTRACT

The present invention relates to a new process of extracting tetrodotoxin from the tissues of an organism. The invention provides increased yield of tetrodotoxin from animal tissues. In the invention, a lixiviated solution is obtained by soaking the tissues with water and a weak organic acid. Soluble proteins are removed by heating the lixiviated solution at a temperature below the boiling point. After pH adjustment, the solution is passed through a cation exchange column. Inorganic salts and alkaline amino acids are removed, and then the tetrodotoxin is adsorbed and eluted from activated carbon. The tetrodotoxin is crystallized by adjusting the pH to 8–10.

18 Claims, 15 Drawing Sheets

METHOD OF EXTRACTING TETRODOTOXIN

FIELD OF THE INVENTION

The invention relates to a new technology of extracting tetrodotoxin from the tissues of organisms, including but not limited to puffer fish. The invention can increase the yield of tetrodotoxin from puffer fish at least three times over that of methods of prior art.

BACKGROUND OF THE INVENTION

Tetrodotoxin is a nonprotein neurotoxin that is found in multiple diverse animal species, including puffer fish, goby fish, newt, frogs and the blue-ringed octopus.

Tetrodotoxin can be obtained from a variety of organisms. The puffer fish, especially its ovaries, is the most well-known source of tetrodotoxin. Tetrodotoxin has also been isolated from species of frog (J. W. Daly et al., *Toxicon* 32:279 (1996)) and in goby fish (T. Noguchi et al., *Toxicon* 11:305 (1973)). It has been hypothesized that colonizing bacteria may be responsible for tetrodotoxin biosynthesis in marine organisms (J. W. Daly, 1996).

The known methods for extraction and purification of tetrodotoxin optimally provide 1 to 2 grams of tetrodotoxin from 100 kg of puffer fish ovaries.

The chemical name of tetrodotoxin and other related data are shown below:

Chemical name: Octahydro-12-(hydroxymethyl)-2-imino-5, 9:7,10a-dimethano-10aH-[1,3]dioxocino[6,5-d]pyrimidine-4,7,10,11,12-pentol
Molecular formula: $C_{12}H_{17}N_3O_8$
Molecular weight: 319.27

Structure:

Pure tetrodotoxin is a colorless crystalline powder. It darkens above 220° C. without decomposition. There are several hydrophilic hydroxyl groups in tetrodotoxin, making it insoluble in organic solvents. Its molecular skeleton is similar with the cage structure of adamantane, making hydration very difficult, thus it is just slightly soluble in water. Because there is a guanidine perhydroquinazoline group in the molecule, and guanidine group is strongly alkaline, tetrodotoxin is soluble in water solutions of acids. Because tetrodotoxin also has the structure of inner ester, and water solutions of strong acid will make it decompose, the only way to keep it stable in solution is to dissolve it in a solution of weak organic acid. The particularity of C-4 can be easily seen from the molecular structure of tetrodotoxin. C-4 is in the ortho-position of the nitrogen atom with OH group at equatorial position and H atom at axial position. Therefore, the chemical and biological activities of the hydroxyl group on C-4 are significant. If H+ is present in the solution, the oxygen atom from the hydroxyl group of C-4 will combine with it, and produces positively charged structure B from structure A. Structure B losses a H20 molecule and result in structure C with positively charged C-4.

Structure C may interact with $H_2O$ in the solution. The $H_2O$ can either attack the position where the original $H_2O$ molecule is eliminated so that structure E is derived, or attack the opposite position where the $H_2O$ molecule is eliminated so that structure D is derived. If a $H_2O$ molecule is removed from structure E, the original tetrodotoxin structure A is produced. Structure D will lead to structure F after a $H_2O$ is removed. The difference between structure F and A is that the positions of H and OH are exchanged. The H on C-4 of structure A is axial and OH is equatorial, while in structure F the H on C-4 is equatorial and OH is axial.

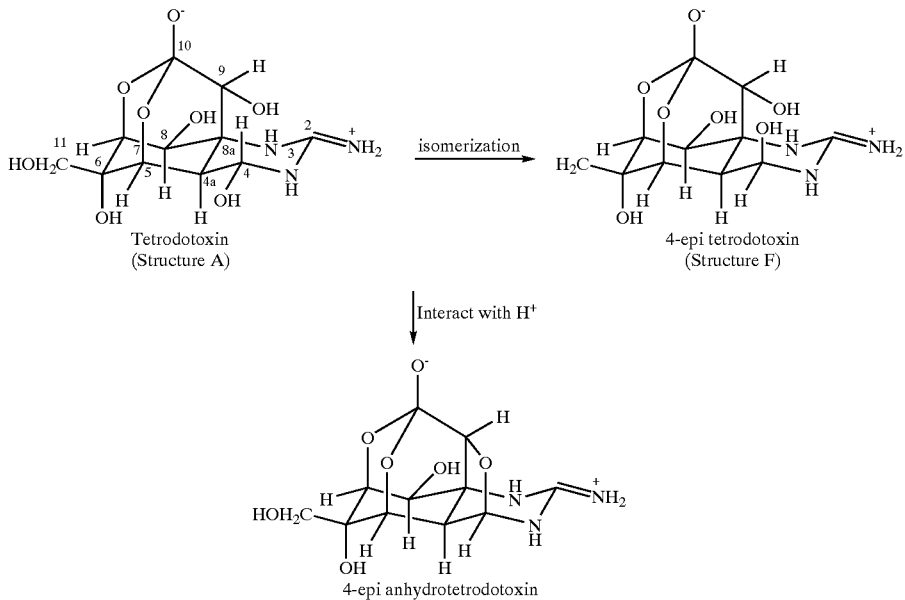

Tetrodotoxin (Structure A)

4-epi tetrodotoxin (Structure F)

4-epi anhydrotetrodotoxin

Tetrodotoxin structure A is called “tetrodotoxin”, which is the predominant content of tetrodotoxin (TTX) obtained from puffer fish in the nature. Tetrodotoxin structure F is usually called 4-epi tetrodotoxin. Because the hydroxyl group on C-4 is close to the one on C-9 in 4-epi tetrodotoxin, a $H_2O$ molecule is easily removed under the interaction of $H^+$, resulting in an analog of tetrodotoxin containing ether bond, which is called 4-epi anhydrotetrodotoxin. The chemical properties of these three “tetrodotoxin” molecules are only slightly different. But they have significant differences in terms of biological activities. For example, the toxicity of tetrodotoxin is 4500 mouse units/milligram; 4-epi tetrodotoxin, 710 mouse units/milligram; 4-epi anhydrotetrodotoxin, only 92 mouse units/milligram (*Toxicon,* 23 271--276(1985)).

The importance of C-4 hydroxyl group is also manifested in that its toxicity will be substantially reduced when it is replaced by other groups, such as H, $CH_3$ or $CH_3CO$—. Hence, theoretically, efforts should be made to keep the hydroxyl group on C-4 equatorial during the extraction of tetrodotoxin. So it is very important to select the right extraction devices and materials, pH and temperature of the solution, and time for the extraction process. The toxin extracted from puffer fish is a mixture that consists of more than 10 analogs, predominant among which is tetrodotoxin, accounting for 70% to 80% of the mass of the extract. Three other major analogs are tetrodonic acid, 4-epi tetrodotoxin and 4-epi anhydrotetrodotoxin, which are only slightly different in chemical properties but significantly different in biological activities. For example, the toxicity of tetrodotoxin is 4500 mouse units/milligram; 4-epi tetrodotoxin, only 710 mouse units/milligram; 4-epi anhydrotetrodotoxin, dramatically decreased to 92 mouse units/milligram (*Toxicon,* 23, 271–276(1985)).

Two approaches, synthesis and extraction from biological sources, have been used to obtain tetrodotoxin. In 1972 Y. Kishi et al succeeded in completely synthesizing tetrodotoxin. At the beginning of the 20th century, Tahara in Japan started extracting tetrodotoxin (*J. Pharm. Soc. Japan* 29. 587(1909), *Biochem.Z.*30 255(1911)). He used lead acetate and aqueous ammonia to precipitate toxin and lead together, then removed the lead by treatment with hydrogen sulfide. Tahara further added methanol and diethyl ether to the filtrate after removal of the lead, and finally precipitated the toxin. Tahara measured the toxicity of the crude toxin to be 4.1γ, (The mean lethal dose to 1 gram of mouse is MLD 4.1γ/g, abbreviated as 4.1γy), and named the toxin as “tetrodotoxin”, as the toxin is called today. In the decades following, many extraction methods were developed; representative methods are:

In 1950, Yokoo successfully obtained crystalline toxin of MLD 0.01γ (*J. Chem. Soc. Japan* 71, 590 (1950)). He obtained the ovaries from the puffer fish caught near Shimomi, Japan at the end of January, lixiviated them in water and steamed the product dry. The result was a dry substance of MLD 40γ. Next, lead acetate and ammonia were used to precipitate toxin and lead together, then the impurities were removed with phospho-tungstic acid and mercury picrate; sugars were removed with phenyl hydrazine. Mercury picrate was used again to treat the precipitate, followed by treatment with picrolonic acid, methanol, and picrolonic acid so that crystalline toxin of MLD 0.8γ was obtained. But out of 20 kg of ovaries, Yokoo obtained only 13 mg crystalline toxin.

In 1951, Nagai (*Fukuoka Ishi* 45, 1 (1954)) used ion exchange resin (Amberlite IRC-50) to adsorb toxin, eluting with hydrochloric acid, then treating the eluate with Amberlite IR-4B to remove hydrochloric acid. After concentration, anhydrous alcohol was used to extract toxin. 2.5 mg toxin crystals of MLD 0.008γ were finally obtained from 20 kg of the puffer fish ovaries.

In 1952, Tsuda and Kawamura used circular filter paper chromatography (K. Tsuda et al, *J. Pharm. Soc. Japan* 72, 187, 771(1952)) and obtained toxin of MLD=10 μg/kg. Later they developed a method for mass production by active charcoal column chromatography (Tsuda, Kagaku no Ryouiki, supplement, 80, 9 (1967)), which was capable of processing 1000 kg of ovaries and obtained 10 grams toxin with MLD=10 μg/kg. Meanwhile, Woodward (R. B. Boodward, Pure Appl. Chem. 9, 49–74 (1964)) achieved similar results.

In 1964, Goto Toshio et al (Goto Toshio and Takahashi et al., J. Chem. Soc. Japan 85, 508 (1964)) simplified the technological process by using ion exchange and active charcoal adsorption (See FIG. 1). They obtained 1–2 grams so-called crude toxin from 100 kg of ovaries.

After 1980, some methods were reported from time to time but they generally followed T. Goto's method and failed to increase yield.

This invention makes significant improvements with respect to the yield-restraining factors that have been discovered by the inventors after years of research on the advantages and deficiencies of existing extraction technologies. The yield of tetrodotoxin by this invention is at least three times that previously reported in the literature.

SUMMARY OF THE INVENTION

The extraction of tetrodotoxin of this invention comprises five steps as follows:

Step 1

Grind the tissues into small pieces, soak with an amount of water equal to 1.5 times by weight of the tissues and an amount of a weak organic acid, typically a carboxylic acid, preferably acetic acid, equal to 0.05%–1%, preferably 0.1%–0.3%, by weight of the tissue for several hours, then stir and filter quickly to obtain a lixiviated solution. Repeat this step 3–4 times in order to extract as much toxin as possible.

Step 2

Heat the lixiviated solution to 70–95° C. to coagulate and remove soluble proteins ("scleroprotein").

Step 3

Adjust the pH of the lixiviated solution obtained in step 1 to 6.0~7.5 using an aqueous solution of a weak base, then put the solution through a weakly acidic cation ion-exchange resin to enrich tetrodotoxin. Elute the bound tetrodotoxin with a weak acid.

Step 4

Adjust the pH of the obtained tetrodotoxin solution in step 3 to 8 to 9 for a period of 2–4 hours, during which put the solution through a column filled with active charcoal and diatomaceous silica so as to remove inorganic salts and a fraction of the alkaline amino acids. Then wash the column with de-ionized water first, then with acidic ethanol solution, in order to elute as much toxin adsorbed as possible.

Step 5

Purify and crystallize tetrodotoxin by concentrating the solution obtained in step 4 under vacuum, then adjusting to an alkaline pH. Vacuum dry the obtained tetrodotoxin crystals, typically about 24 hours until the weight of the crystals becomes constant.

DETAILED DESCRIPTION OF THE INVENTION

Figure 1:
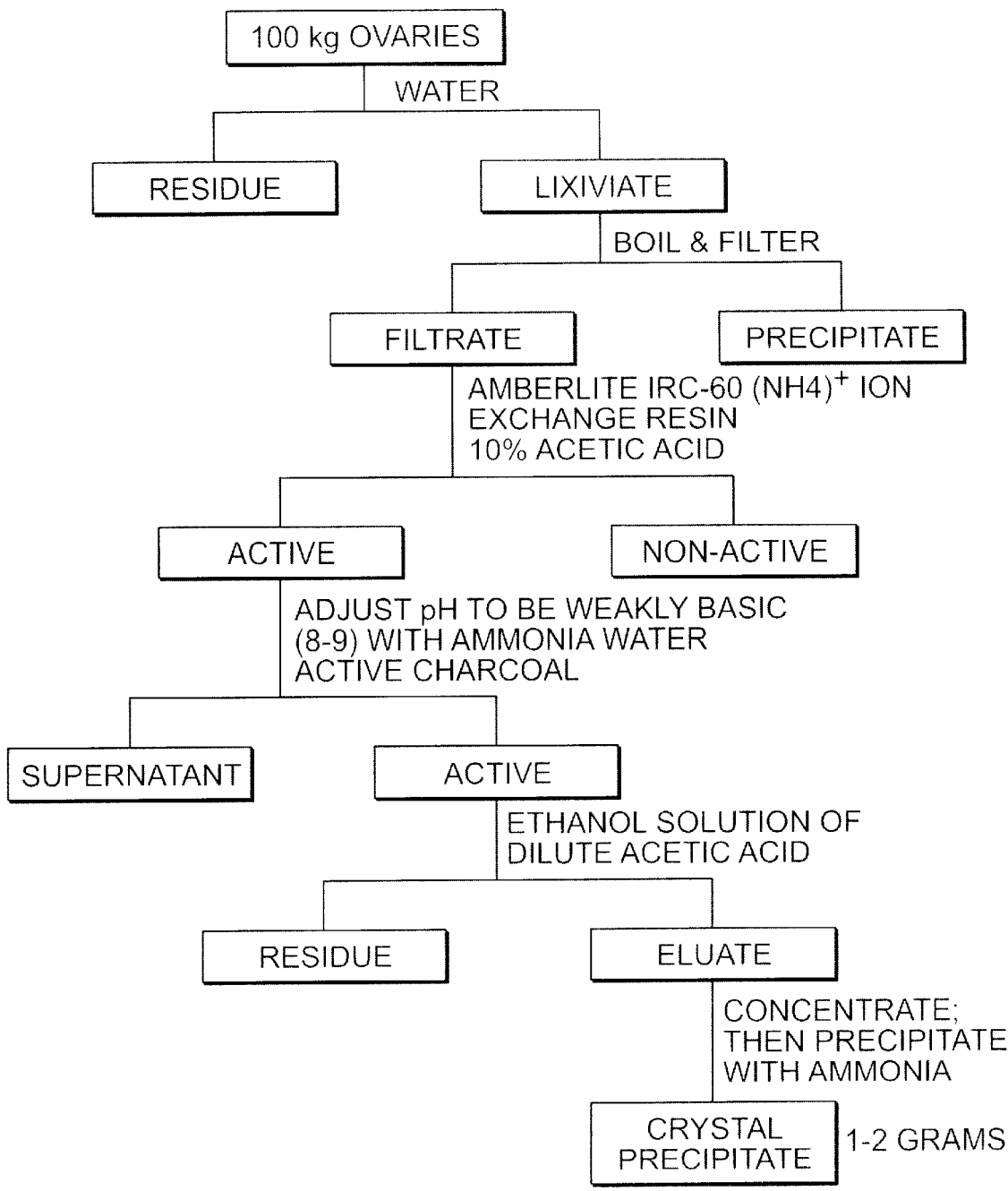
FIG. 1: (Prior Art) Flow chart of extraction method of T. Goto.
Figure 2:
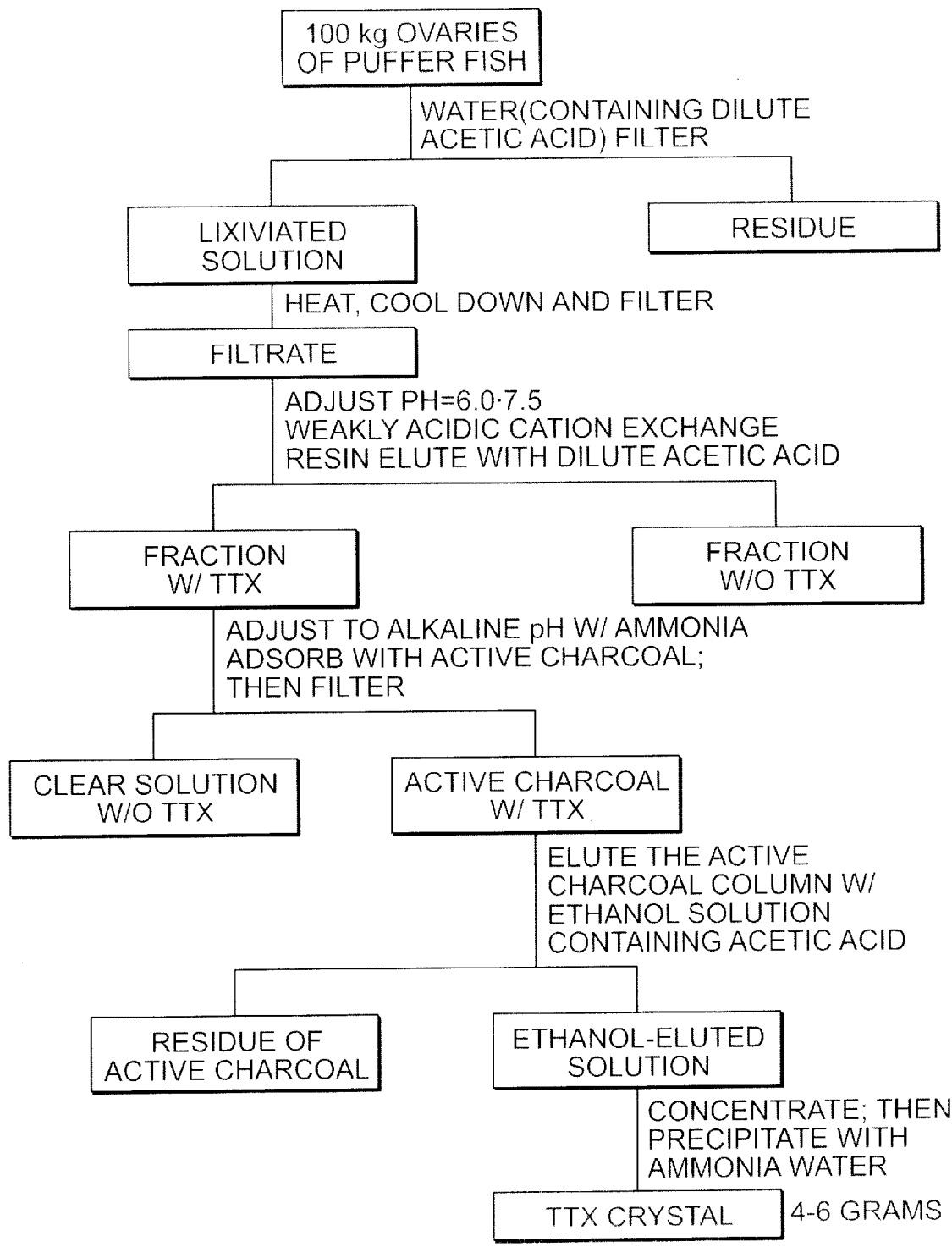
FIG. 2: Flow chart of the extraction method of the invention.
Figure 3:
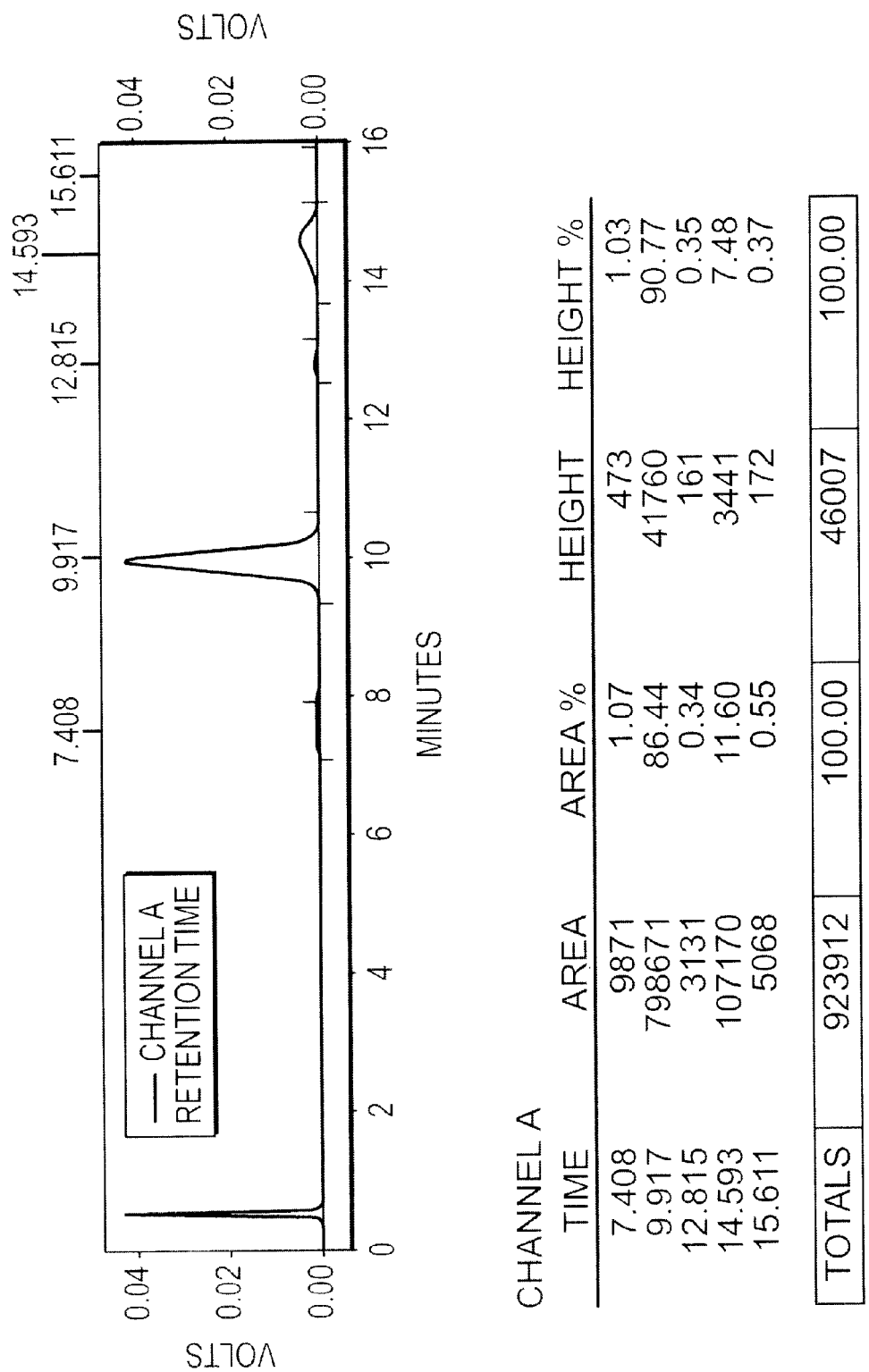
FIG. 3: HPLC profile of crystalline TTX obtained in Example 1.

The following general procedures should be followed to extract tetrodotoxin from animal tissues with high yield. Tissues of puffer fish, preferably the ovaries, are a preferred source of tetrodotoxin.

1. Lixiviation with Water

Grind the tissue into pieces less than 1 cubic cm, put into a container, and add de-ionized water in an amount equal to 1.5 times by weight of the tissue, then add acetic acid weighing 0.05~1%, preferably 0.1–0.3%, by weight of the tissue to extract TTX from the tissue more efficiently. Stir for a few hours at room temperature. Filter the liquid using nylon filtering material with a pore size of 100–200 meshes per square inch and stainless steel mesh of 40–60 meshes per square inch. Collect the filtrate, heat quickly to 70–95° C. for about 3–25 minutes. Cool down and filter out the scleroprotein that has been separated out, so a yellow transparent liquid is obtained and called first lixiviated clear liquid.

Inject intraperitoneally 0.4 mL of the first clear lixiviated liquid into a mouse having a body weight of 20 grams. The tissue will be determined to be extremely toxic raw material if the mouse dies within 50 seconds; or highly toxic raw material if between 50~70 seconds; or mildly toxic raw material if between 70~90 seconds. The lixiviated liquid that causes such a mouse to die after more than 90 seconds is considered not qualified for extraction.

Add de-ionized water to the residue of the first lixiviation, stir for several hours, and repeat the same lixiviation process, filter, heat, filter, and collect the second lixiviated liquid. Repeat the lixiviation process to obtain the third and the fourth lixiviated liquids. The fourthly lixiviated liquid is to be collected only when extremely or highly toxic tissues are used. The fractions of lixiviated liquid are pooled. For mildly toxic ovaries, only up to the third lixiviated liquid is used. Pool all the lixiviated liquid fractions that meet the bioassay criterion (lixiviated clear liquid). Determine the toxin content of the pooled lixiviated clear liquid by bioassay or high performance liquid chromatography (HPLC).

2. Ion-Exchange Enrichment and TTX-Separation Process

Use a weak base, preferably an aqueous amine, for example aqueous ammonia, to adjust the pH of the clear lixiviated liquid to between 6.0 and 7.5 so as to remove neutral and acidic amino acids from the liquid. Filter if there is any precipitate. Put the clear lixiviated liquid through a weakly acidic cation-exchange resin column at an outflow speed of 100~190 mL/hr per kilogram of tissue used. The effluent solution can be monitored by thin layer chromatography (TLC) using a silica gel thin-layer plate eluted with n-butanol: acetic acid: water (2:1:1). TTX can be detected by spraying the plate with 10% KOH solution after it is eluted, baking for 10 minutes at 110° C., and observing under a 365 nm ultraviolet lamp. TTX is detected as blue fluorescent spots with $R_f$=0.38–0.40. If toxin leaks, the resin column must be replaced with a new one immediately.

After all of the clear lixiviated liquid passes through the column, wash the column with de-ionized water until no scleroprotein is present in the wash outflow. Then wash the column with a solution of 5 to 12% acetic acid with a flow rate of 25~125 mL/hr per kilogram tissue used. Collect the eluate in 1500 mL portions, and check the toxin content of each portion using the TLC method. Pool those portions that are determined by the TLC method to contain toxin.

3. Purification with Active Charcoal

The portion of the eluate containing TTX is pooled and the pH of the pooled solution is adjusted to between 8 and 9 with a weak base, typically an amine, preferably concentrated.aqueous ammonia, and the pH is maintained for a period of 2–4 hours, during which time the solution is passed through a column packed with active charcoal and diatomaceous silica. The column is packed in two layers, where the diatomaceous silica layer is placed above the active charcoal layer and has a thickness of 1/10 to 1/2, preferably 1/10–1/5, the thickness of the active charcoal layer.

The column is washed with de-ionized water, then washed again with an ethanol solution that contains acid (the concentrations of the ethanol and acid are between 0.5%~40%, preferably 15%–30%, ethanol and 0.2–0.6% acetic acid) so that the toxin adsorbed can be eluted as much as possible (TLC as described above can be used to monitor the eluate for TTX content).

4. Concentration and Crystallization

The eluate containing TTX washed from the active charcoal-diatomaceous silica column is cooled and the pH of the solution is adjusted with a weak base, preferably an amine, typically aqueous ammonia to between 8 and 9, and left standing to precipitate TTX. The TTX precipitate is collected by filtration and then washed with de-ionized water several times, dried and dissolved in acetic acid. The TTX is reprecipitated by adding aqueous ammonia. The recrystallization is preferably repeated. The obtained TTX crystals are dried under vacuum, typically for 24 hours so that the weight of the crystals becomes constant. High performance liquid chromatography can be used to determine the content of the crystals.

EXAMPLES

The following examples serve to illustrate the invention, but are in no way intended to limit the invention.

Ovaries of puffer fish are used as the starting tissue in these examples. The ovaries used were determined to be extremely toxic by bioassay and contained tetrodotoxin at 10–15 milligrams per liter lixiviated clear liquid.

Example 1

Twenty kilograms ovaries of puffer fish were ground into pieces less than 1 $cc^3$, and put into a container. Thirty liters de-ionized water and 30 milliliters acetic acid were added. The mixture was stirred for 10 hours at room temperature. Next, the solution was filtered using nylon filtering material with a pore size of 100 meshes per square inch and stainless steel mesh of 40 meshes per square inch. After filtering, another 30 liters de-ionized water was added to the remained ovaries and the lixiviation process was repeated. The lixiviation process was repeated for a total of four times where the aforementioned bioassay criterion was met.

The filtrates each were heated at 80° C. for 5 minutes and cooled down. The resulting scleroprotein was separated out so that lixiviated clear liquids were obtained.

The clear lixiviated liquids were pooled into one solution, the pH of which was adjusted to 7.5 using aqueous ammonia. Then the solution was put through a weakly acidic cation exchange resin column. The column had a height of 1 meter and a diameter of 6 centimeters, and was filled with D-152 resin manufactured by Nankai University Chemical Factory, Tianjing, P.R. China. After the solution all passed through, the column was washed clean with de-ionized water, then was eluted with 10% aqueous acetic acid solution to get a TTX eluate. Subsequently, strong aqueous ammonia was used to adjust the pH of the TTX eluate to 8.5. The resulting solution was put through an active charcoal-diatomaceous silica column, where a diatomaceous silica layer is placed above an active charcoal layer. The diatomaceous silica layer is 1/15 the thickness of the active charcoal layer. The TTX was adsorbed on the active charcoal. A 20% aqueous ethanol solution of 0.2% acetic acid was used to elute TTX, and the eluate was put into a rotating evaporator to concentrate to about 15 milliliters. After being cooled down, the pH of the concentrated solution was adjusted with concentrated ammonia to 9, and the solution was put into a refrigerator to be cooled further and to crystallize TTX. The crystals were filtered and dissolved in 5% acetic acid, then the pH of the resulted solution was adjusted with strong ammonia to 9, and TTX in the solution was crystallized and precipitated again. Then the TTX crystals were placed in a vacuum drier and were dried for 24 hours so that their weight became constant. The TTX content of the dried product was determined by high performance liquid chromatograph (HPLC) to be 86.17% (See FIG. 3). The HPLC method used a Beckman HPLC (USA, including Model 125 pump. Model 166 variable wavelength detector and Gold Nouveau chromatography workstation) . The reagents used in the HPLC measurement include heptane sodium sulfonate (KASEI KOGYO CO. LTD., Tokyo, Japan), methanol (Merck) and deionized water. The sample can be prepared by accurately weighing 10 mg of tetrodotoxin product into a 25 ml volumetric flask, adding 0.02% acetic acid solution, diluting to the mark, and shaking to mix well. Injection was 20 $\mu$l of the solution into the HPLC. The measurement conditions were column: ODS (5 $\mu$m), 4.6 mm×250 mm; column temperature: 30° C.; mobile phase: 0.01 mol/L heptane sodium sulfonate (pH 5.30) —Methanol (100:1); flow rate: 1.5 ml/min; and detection wavelength: 205 nm.

From 20 kilograms ovaries, 1200 milligrams TTX crystals were obtained, an equivalent of 6.0 grams per 100 kilograms ovaries. This yield is three or more times higher than that by any previous method.

For mass spectrometric analysis, 50 $\mu$g of the crystalline TTX were dissolved in 50 $\mu$l of acetic acid. The sample was then directly injected into a Bruker APEX™Fourier transform mass spectrometer. Ionization was by fast atom bombardment. Peaks at m/z of 302 and 320 were observed having relative abundance of 18.6 and 100, respectively.

Example 2

Twenty kilograms toxic ovaries of puffer fish were ground into pieces less than 1 $cc^3$, and put into a container. Thirty liters de-ionized water and 30 milliliters acetic acid were added. They were stirred for 10 hours at room temperature. Then the liquid was filtered using an air pressure differential to drive the filtration. After filtering, another 30 liters de-ionized water was added to the remaining ovaries and the lixiviation process was repeated. The lixiviation process was repeated a total of four times where the aforementioned bioassay criterion was met.

The filtrates were each heated to the boiling point for 10 minutes and cooled down. The resulting scleroprotein was separated out so that lixiviated clear liquids were obtained.

The TTX was further processed as in Example 1. 350 milligrams TTX crystals with a purity of 82% were obtained. The cause for the decrease in the yield is that the filtrates were boiled, following T. Goto's method. The boiling decomposed much of TTX, greatly decreasing the TTX content.

Example 3

The same processes as in Example 1 were performed, using 20 kg of puffer fish ovaries, except that no acetic acid was added along with de-ionized water in the ovaries during the lixiaviation process. The TTX crystals finally obtained had a purity of 82% and a weight of 620 milligrams. The reason for the decrease in the yield is that acetic acid was not added in the lixiviating solution to help dissolve TTX from the ovaries.

Example 4

The same processes as in Example 1 were performed, using 20 kilograms of puffer fish ovaries, except that the pH of the pooled clear lixiviated liquids, being 5.5, was not adjusted to between 6.0–7.5 with aqueous ammonia before they were put through a weakly acidic cation exchange resin column. The TTX crystals finally obtained had a purity of 85% and a weight of 410 milligrams. The reason for the decrease in the yield is that neutral and acidic amino acids exist in the clear lixiviated liquids and cannot be removed under an acidic condition. If the pH is not adjusted; the neutral and acidic amino acids inhibit TTX from being precipitated by ammonia in the next process step.

Example 5

Figure 4:
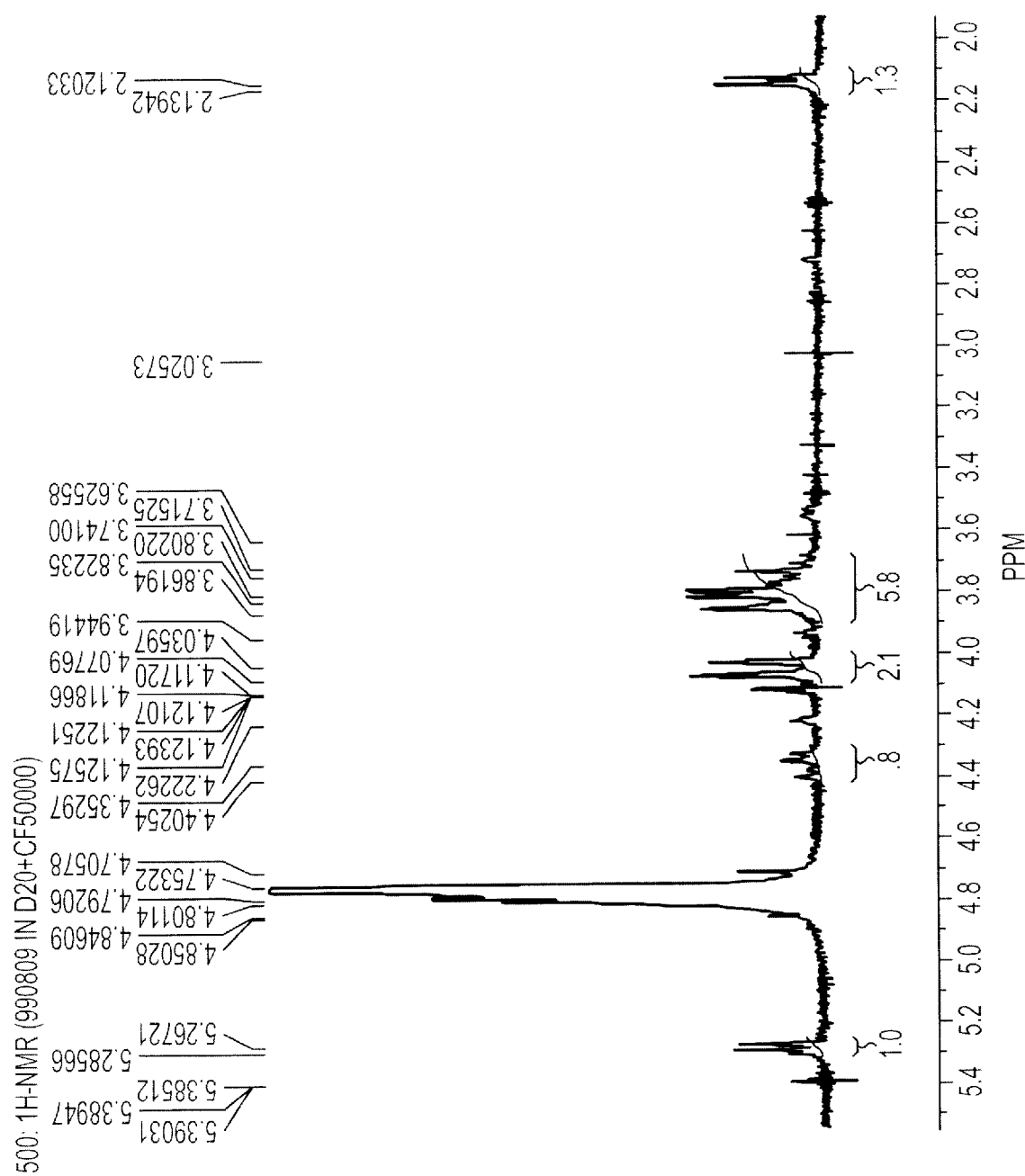
FIG. 4: Proton NMR of crystalline TTX obtained in Example 5.
Figure 5:
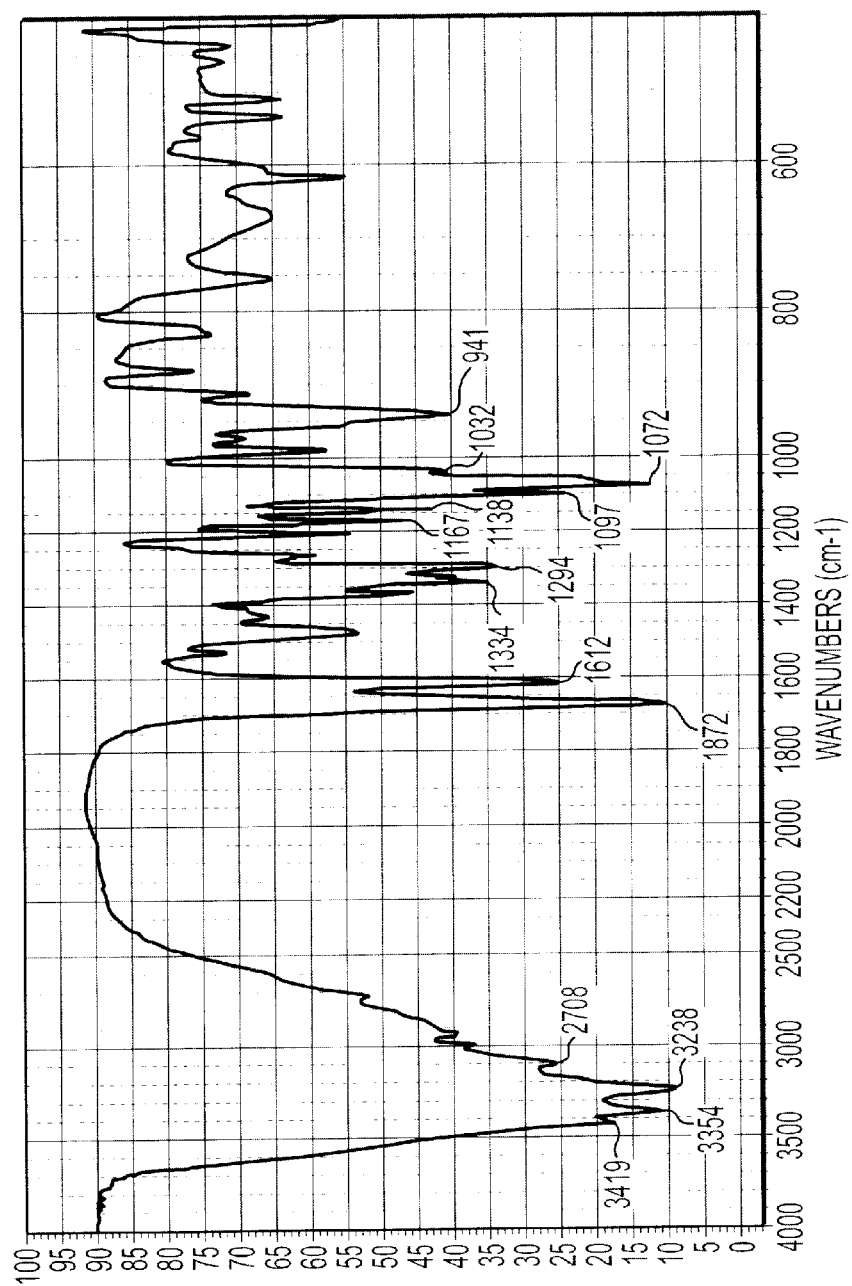
FIG. 5: Infrared absorption spectrum of crystalline TTX obtained in Example 5.
Figure 6:
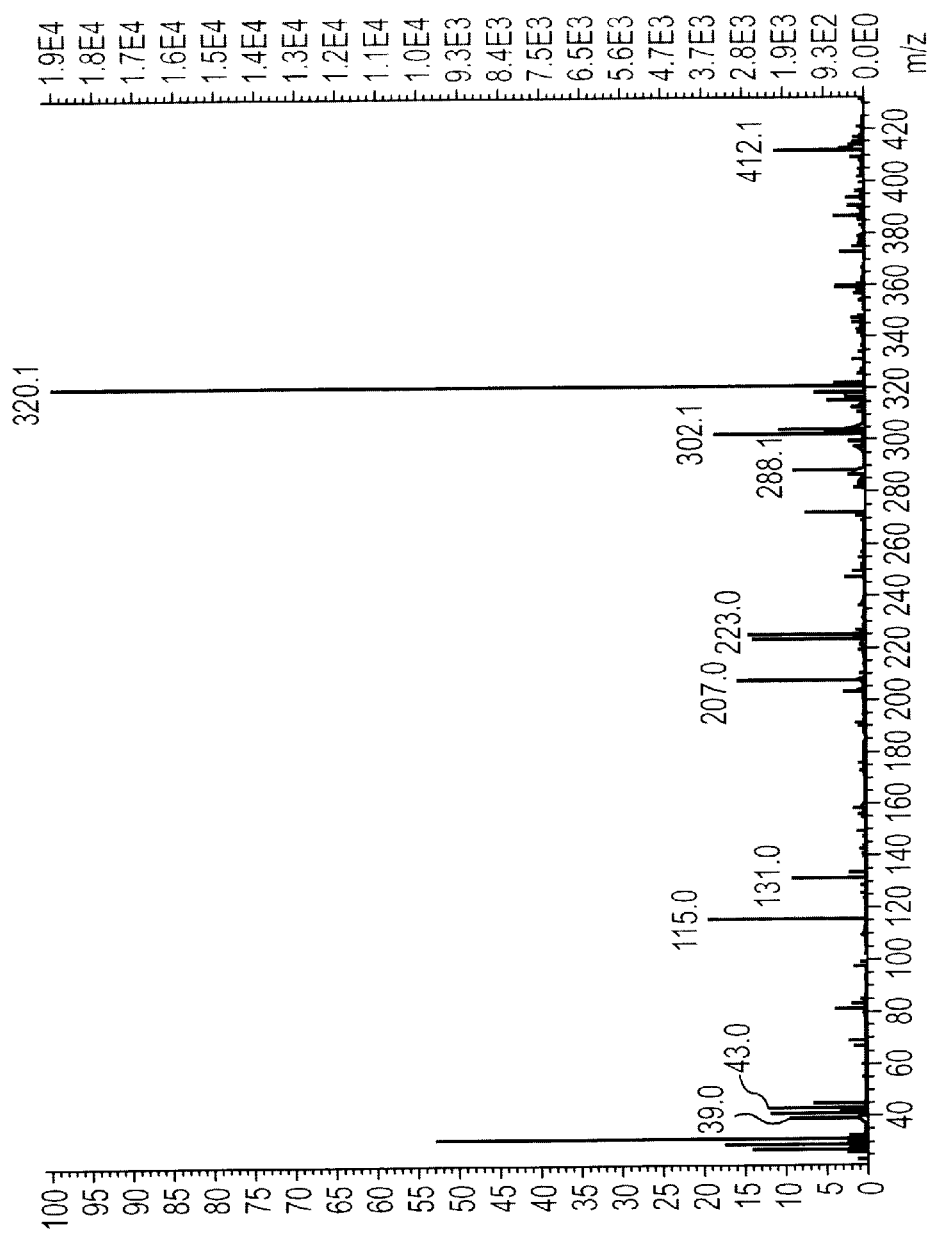
FIG. 6: Mass spectrum of crystalline TTX obtained in Example 5.
Figure 7:
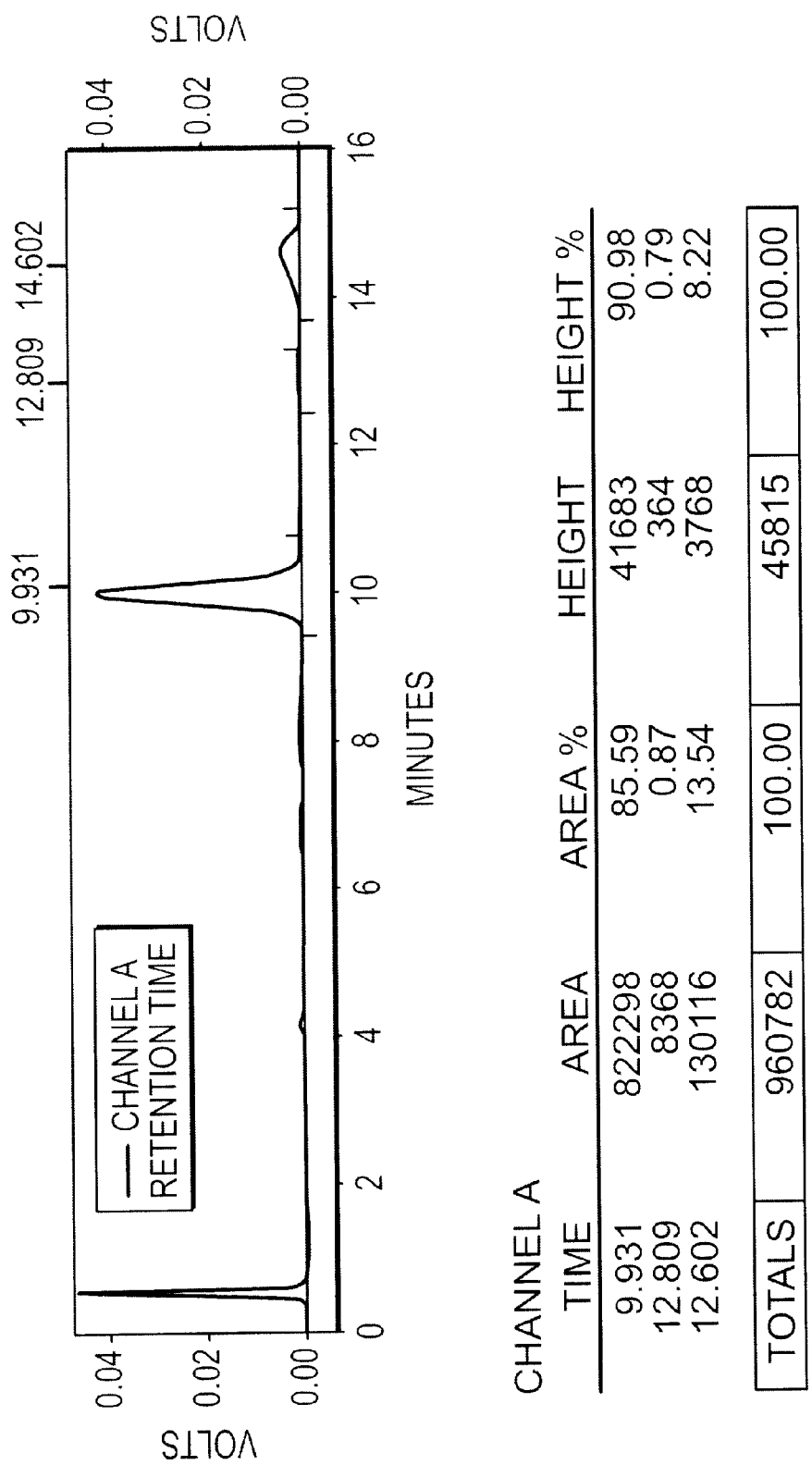
FIG. 7: HPLC profile of crystalline TTX obtained in Example 5.

The same processes as in Example 1 were performed, using 20 kilograms of puffer fish ovaries, except that the heating temperature for the filtrates was controlled accurately to be 90° C., and the heating time was 5 minutes. The TTX crystals finally obtained had a purity of 85.56% and a weight of 1198 milligrams (See FIGS. 4, 5, 6 and 7). The result suggests that the method by this invention will provide a similar yield even if the heating temperature is changed within a certain range under boiling point.

Example 6

Figure 8:
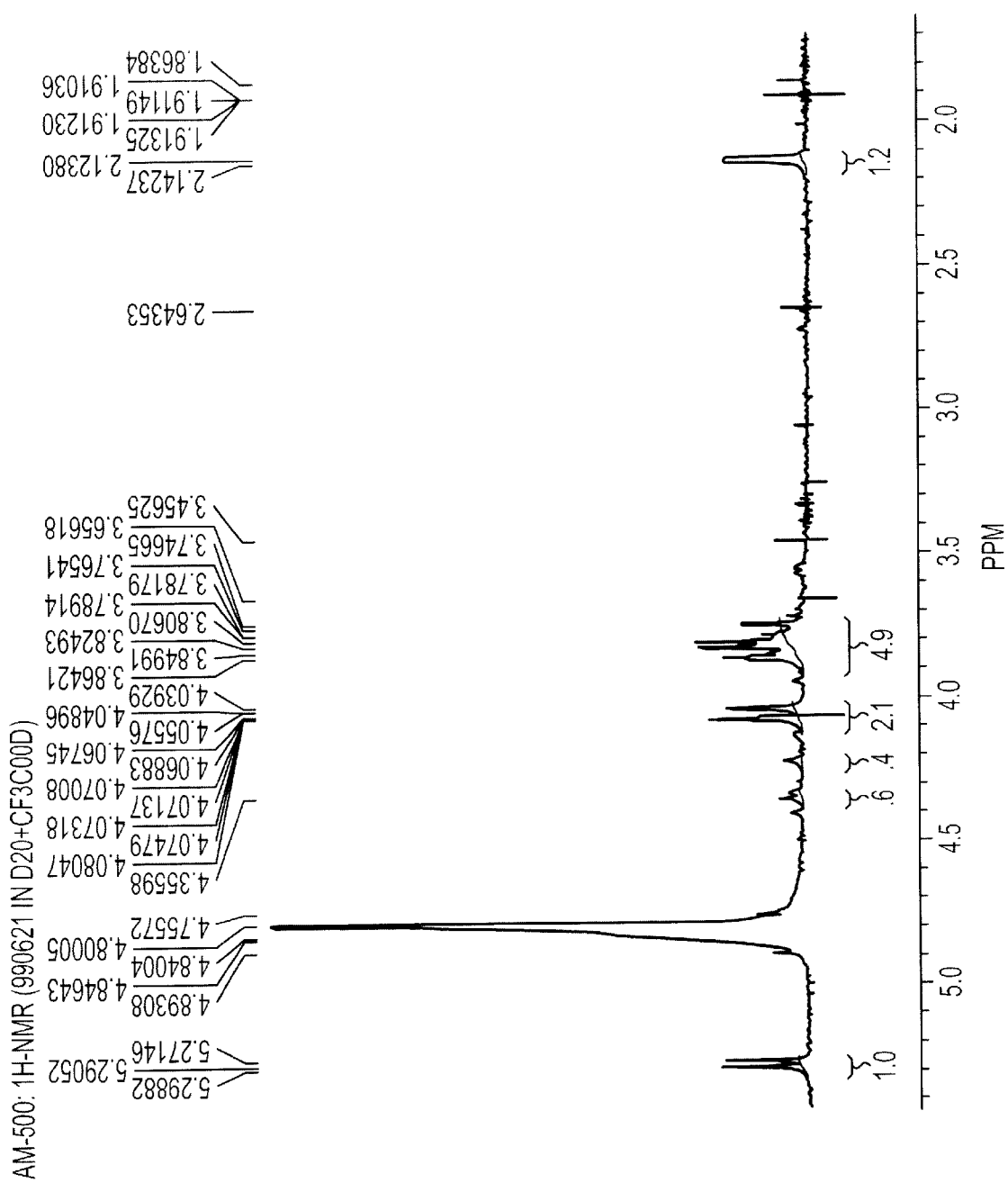
FIG. 8: Proton NMR of crystalline TTX obtained in Example 6.
Figure 9:
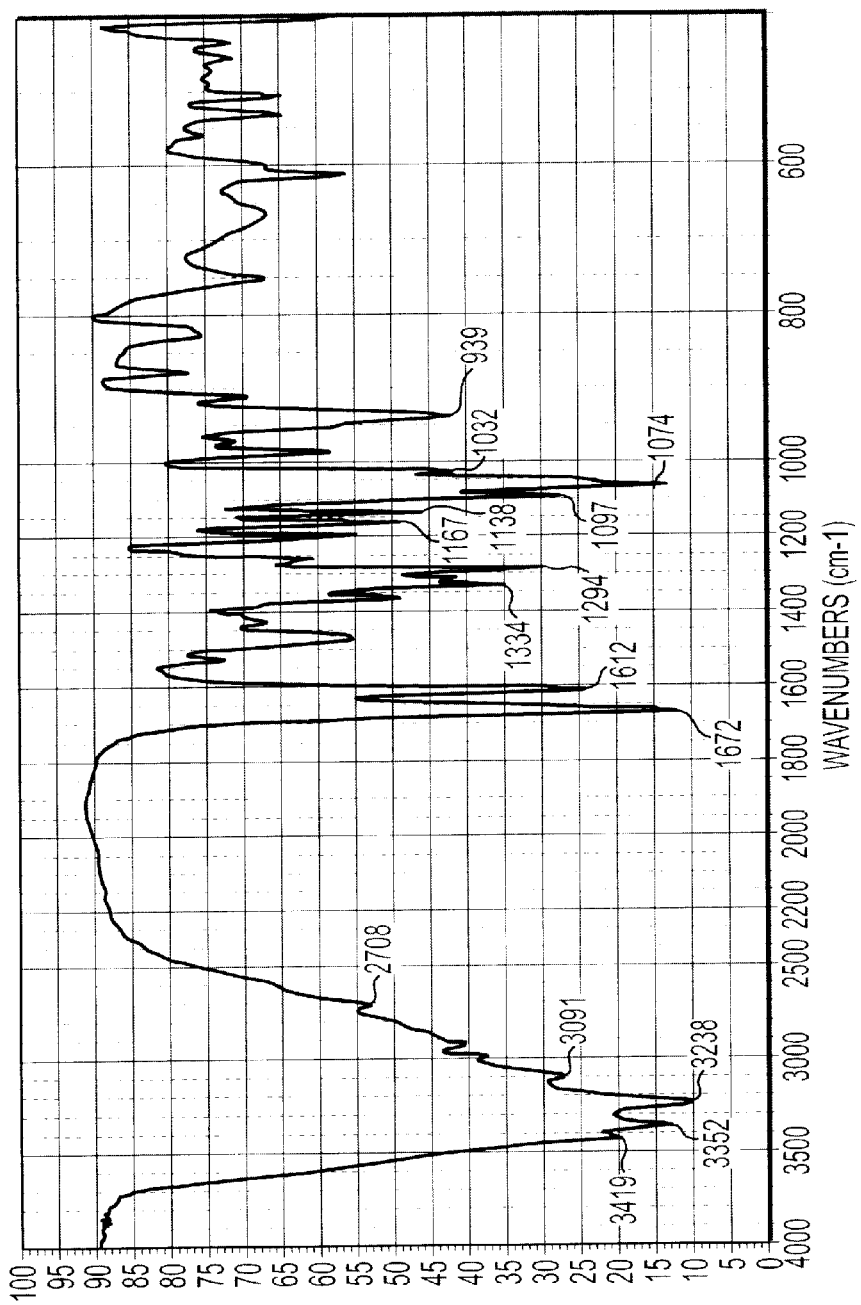
FIG. 9: Infrared absorption spectrum of crystalline TTX obtained in Example 6.
Figure 10:
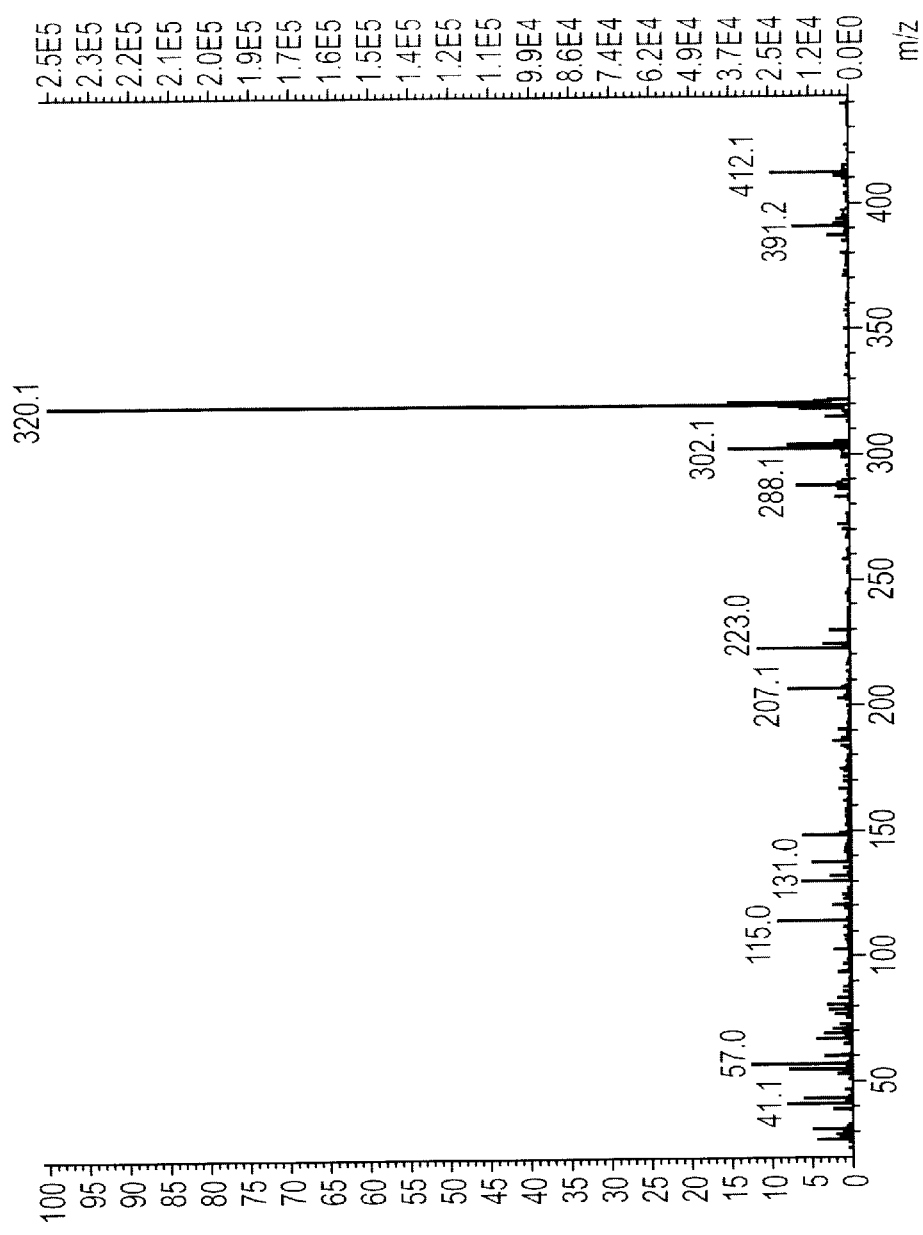
FIG. 10: Mass spectrum of crystalline TTX obtained in Example 6.
Figure 11:
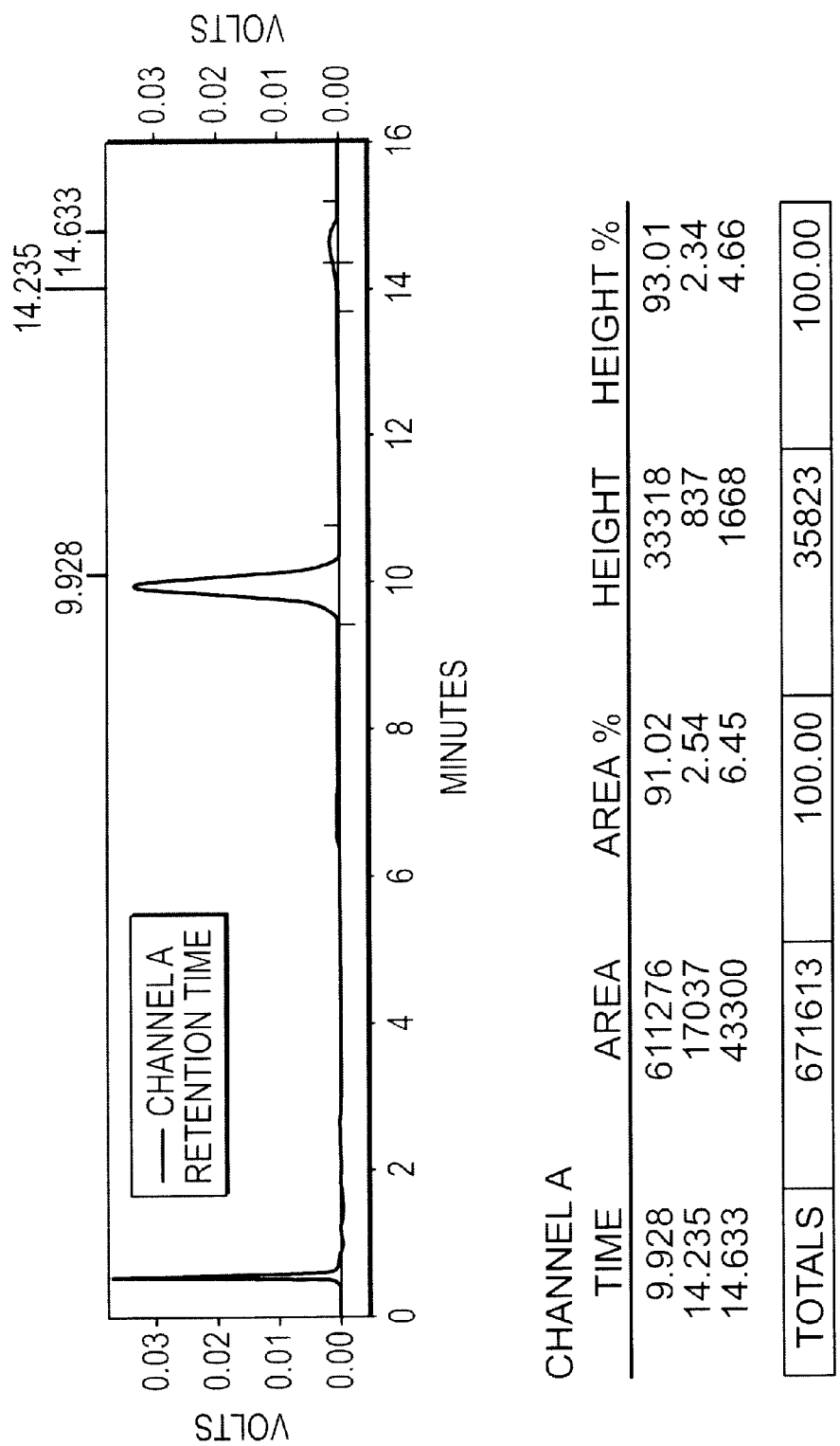
FIG. 11: HPLC profile of crystalline TTX obtained in Example 6.

The same processes as in Example 1 were performed, using 20 kilograms of puffer fish ovaries, except that the ovaries were stirred for 8 hours instead of 10 hours during the water extractions. The TTX crystals finally obtained had a purity of 91.06% and a weight of 1050 milligrams (See FIGS. 8, 9, 10 and 11). The result indicates that the stirring duration may be changed within a certain range without affecting the yield markedly.

Example 7

Figure 12:
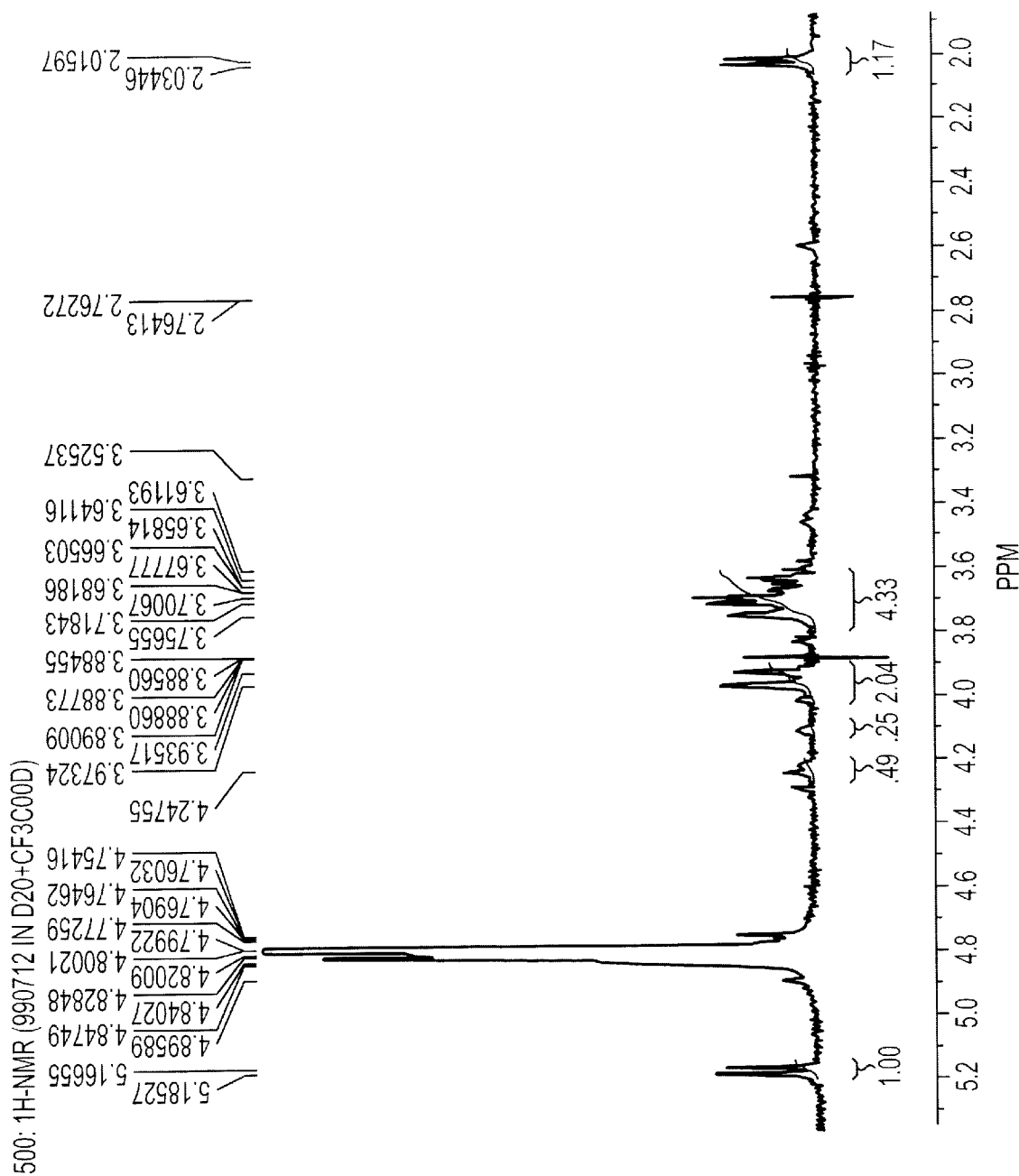
FIG. 12: Proton NMR of crystalline TTX obtained in Example 7.
Figure 13:
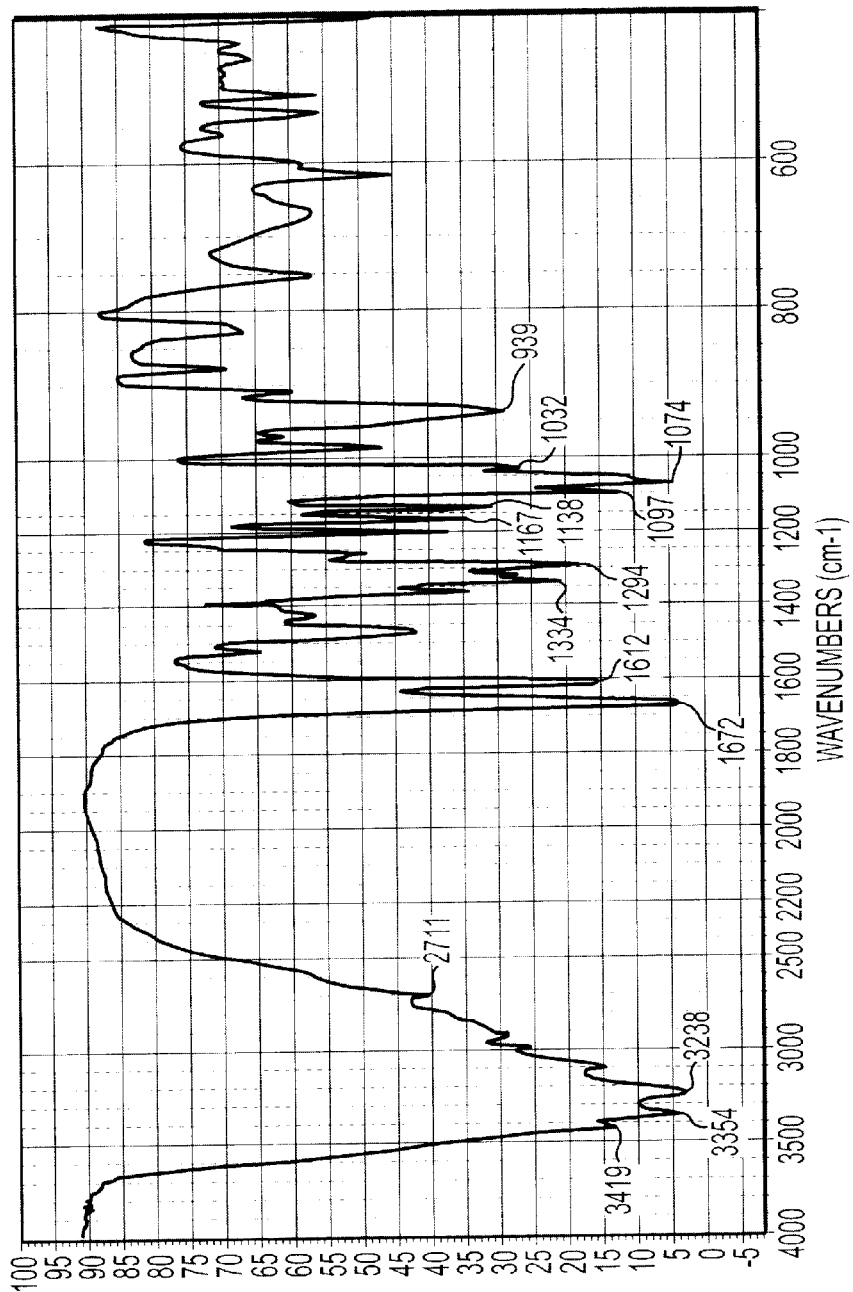
FIG. 13: Infrared absorption spectrum of crystalline TTX obtained in Example 7.
Figure 14:
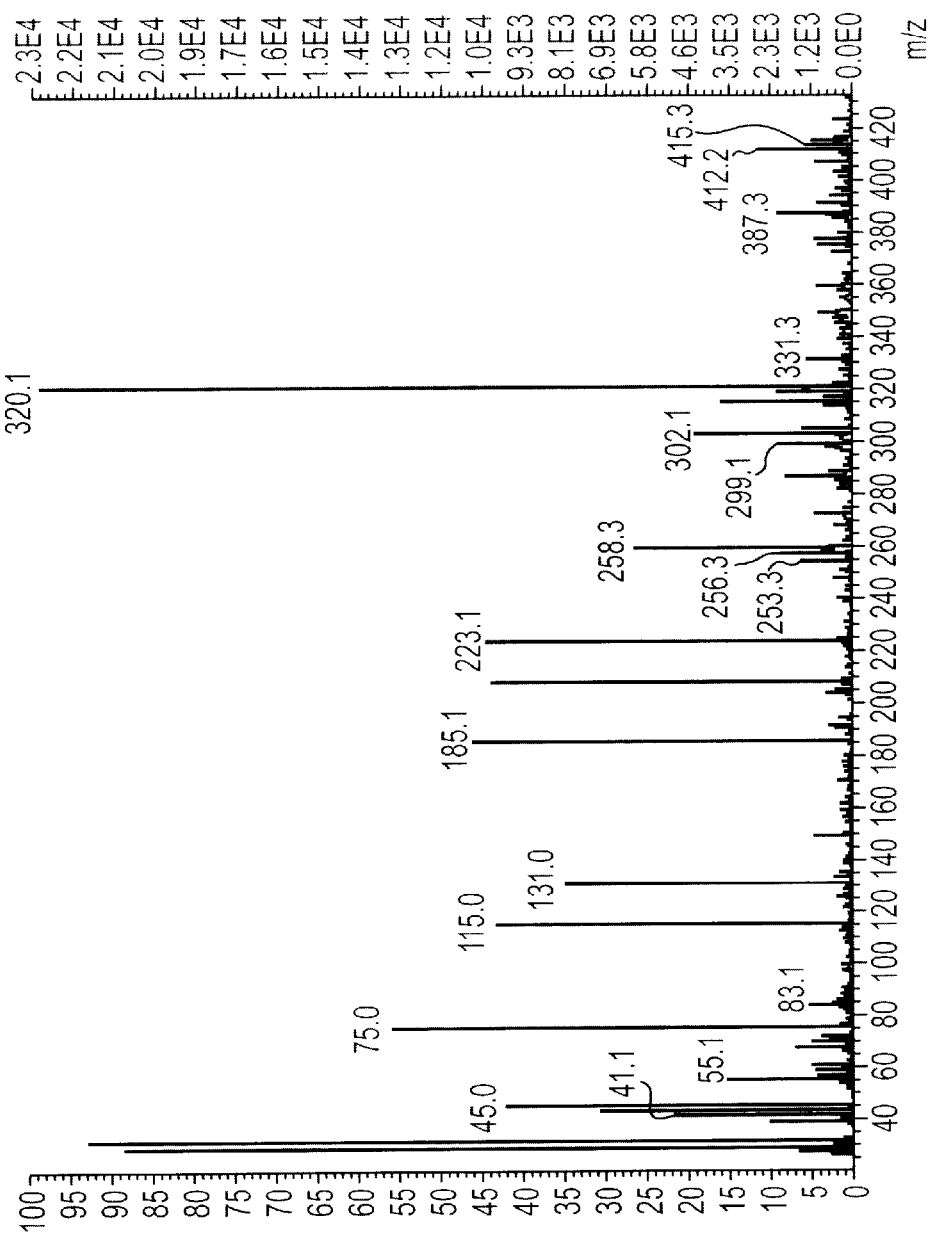
FIG. 14: Mass spectrum of crystalline TTX obtained in Example 7.
Figure 15:
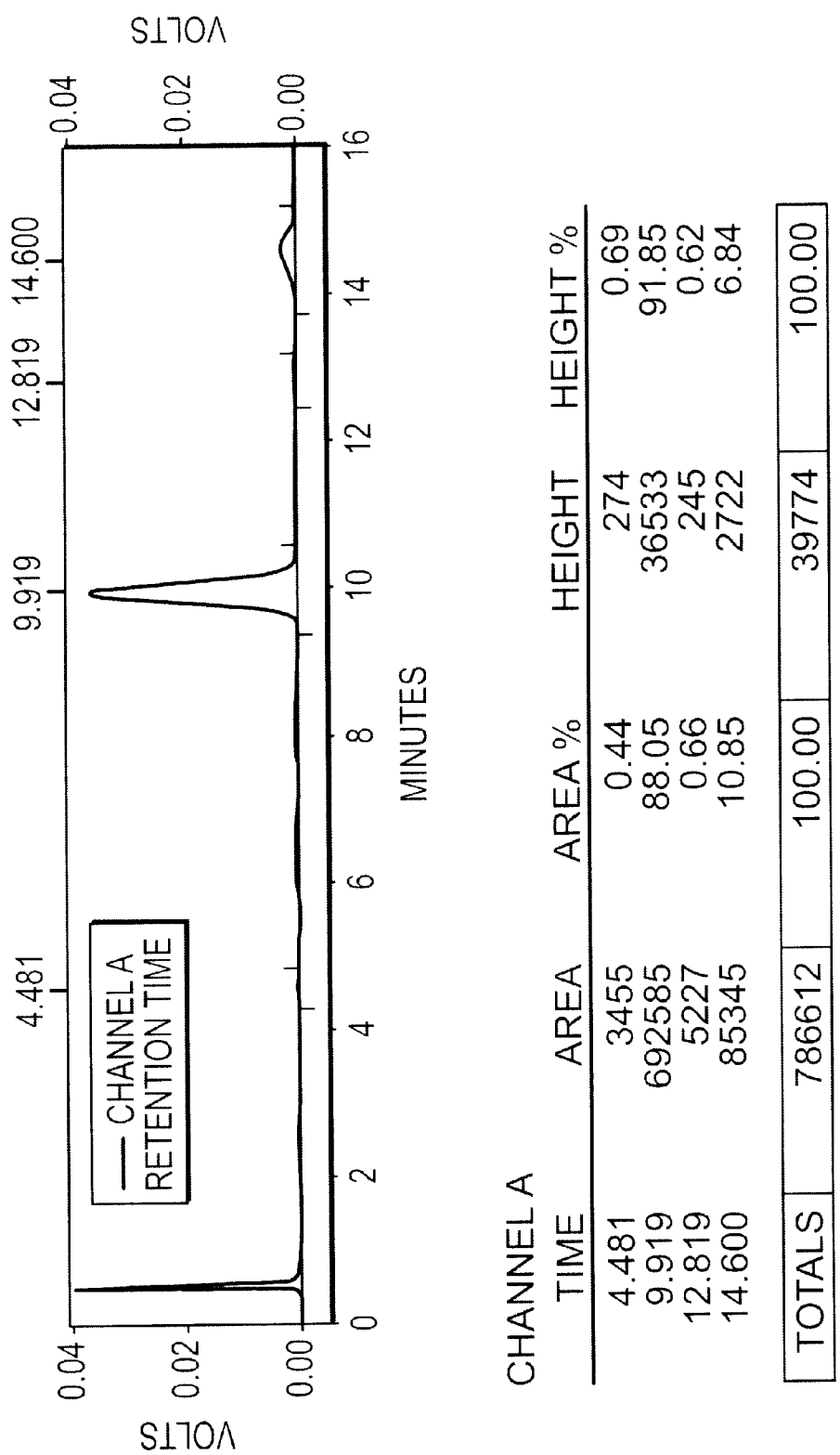
FIG. 15: HPLC profile of crystalline TTX obtained in Example 7.

The same processes as in Example 1 were performed, using 20 kilograms of puffer fish ovaries, except that the filtrates obtained from the lixiviation and filtration process were heated at 70° C. for 25 minutes. The TTX crystals finally obtained had a purity of 88.23% and a weight of 960 milligrams (See FIGS. 12, 13, 14 and 15). The result evidences that the heating temperature and duration may be changed simultaneously within certain ranges without affecting the yield substantially.

REFERENCES

Various articles of the scientific and patent literature are cited throughout this document. Each such article is hereby incorporated by reference in its entirety for all purposes by such citation.

(1).Y. Hirata & T. Goto, Japan Patent No. 290717 (1961), Nihon Kouben Tokyo Kouhou [Showa] 36-13647
(2).Yao-ting Yu, Nihon Kouben Tokyo Kouhou A [Heisei] 3-153627 (1991)
(3).T. Goto, Y. Kishi, S. Takahashi & Y. Hirata, Tetrahedron, 21, 2059–2081 (1965).
(4).Rylji Tachi Kawa Kiyochi Sakai, Ocean Pharm. 4 56–60 (1982)
(5).Muaetomo Nakamuta & Takeshi Yasumoto, Toxicon, 23, 271–276 (1985)
(6).R. B. Woodward, Pure Appl. Chem. 9, 49–74 (1964)

We claim:

1. A method of extracting tetrodotoxin from the tissues of an organism comprising the steps of:
    a) obtaining a lixiviated solution-by soaking the tissues with water and a weak organic acid, then filtering;
    b) removing soluble proteins by heating the lixiviated solution at a temperature below the boiling point;
    c) obtaining an enriched tetrodotoxin solution by adjusting the pH of lixiviated solution with a water solution of a weak base, then putting the solution through a cation ion-exchange resin;
    d) removing inorganic salts and alkaline amino acids by adjusting the pH of the enriched tetrodotoxin solutions with an aqueous solution of a weak base, adsorbing the tetrodotoxin to a activated carbon and eluting the tetrodotoxin from the activated carbon; and
    e) crystallizing tetrodotoxin by concentrating the eluate and adjusting the pH of the eluate to pH from 8 to 10.

2. The method of claim 1, wherein the organism is a puffer fish.

3. The method of claim 2, wherein the tissues are ovaries.

4. The method of claim 1, wherein the weak base is ammonia.

5. The method of claim 1, wherein in step a, the amount of water has a weight from 1.2 to 1.7 times the weight of the tissues.

6. The method of claim 1, wherein in step a, the amount of organic acid has a weight from 0.05 to 1% of the weight of the tissues.

7. The method of claim 6, wherein the amount of organic acid is from 0.1 to 0.3% of the weight of the tissues.

8. The method of claim 1, wherein step a is repeated three to four times.

9. The method of claim 1, wherein step b is accomplished in a period of 3 to 25 minutes.

10. The method of claim 1, wherein step b is accomplished at a temperature from 70 to 95° C.

11. The method of claim 1, wherein step c is accomplished by adjusting the pH to be from 6.0 to 7.5.

12. The method of claim 11, wherein the pH is adjusted to pH 7.0.

13. The method of claim 1, wherein step c is accomplished using a weakly acidic cation ion-exchange resin.

14. The method of claim 1, wherein step d is accomplished by adjusting the pH to be from 8 to 9.

15. The method of claim 1, wherein step d is accomplished by putting the solution through the column within a period of 2–4 hours.

16. The method of claim 1, wherein step e is accomplished by controlling the temperature during the concentrating duration to be from 40 to 50° C., and completing the concentrating within 4 hours.

17. The method of claim 1, further comprising, in step d) filtering the enriched tetrodotoxin solution through diatomaceous silica prior to adsorbing the tetrodotoxin to activated carbon.

18. The method of claim 6, further comprising, in step d) filtering the enriched tetrodotoxin solution through diatomaceous silica prior to adsorbing the tetrodotoxin to activated carbon.

* * * * *